United States Patent [19]

Bruynes et al.

[11] Patent Number: 4,496,720
[45] Date of Patent: Jan. 29, 1985

[54] PREPARATION OF THIOETHERS

[75] Inventors: Cornelis A. Bruynes, Koudekerk an der Rijn; Theodorus K. Jurriens, Delft, both of Netherlands

[73] Assignee: Gist-Brocades N.V., Delft, Netherlands

[21] Appl. No.: 472,667

[22] Filed: Mar. 7, 1983

[30] Foreign Application Priority Data

Mar. 11, 1982 [EP] European Pat. Off. ........ 82200327.3

[51] Int. Cl.³ .................. C07D 501/04; C07C 149/30
[52] U.S. Cl. ....................................... 544/29; 548/110; 548/136; 548/251; 548/265; 548/337; 549/285; 556/426; 560/17; 568/38; 568/41; 568/44; 568/56; 568/57; 568/58
[58] Field of Search .......................... 544/29; 556/426; 548/110, 136, 251, 265, 337; 549/285; 560/17; 568/38, 41, 44, 56, 57, 58

[56] References Cited

U.S. PATENT DOCUMENTS 4,258,195  3/1981  Shibuya et al. ............... 548/110
4,379,923  4/1983  Bruynes et al. ............... 544/21

Primary Examiner—Paul M. Coughlan, Jr.
Attorney, Agent, or Firm—Charles A. Muserlian

[57] ABSTRACT

A novel process for the preparation of thioethers comprising reacting a silylated thiol of the formula $$R\text{—}S\text{—}SiR_1R_2R_3 \qquad \text{I}$$

wherein R is an organic group and $R_1$, $R_2$ and $R_3$ are individually selected from the group consisting of alkyl of 1 to 4 carbon atoms with an organic halide, sulfate or sulfonate in the presence of hexamethylphosphoric triamide as a solvent or co-solvent preferably under neutral conditions in aprotic solvents at a temperature between 0° and 150° C.

10 Claims, No Drawings

PREPARATION OF THIOETHERS

STATE OF THE ART

Several methods for the preparation of thioethers are known; see for example, Oae, Organic Chemistry of Sulfur, Plenum Press, New York, 1977, Chapter 6.

In one method starting with thiols, they are first converted to the corresponding mercaptides, usually by reaction with aqueous or alcoholic solutions of sodium hydroxide or sodium ethoxide and the mercaptides are then reacted with organic halides, dialkyl sulfates or alkyl sulfonates. Accordingly, these reactions are carried out under alkaline conditions in protic solvents which may lead to undesired side-reactions since other functional groups present in the reactants can be effected as well. In another method starting with thiols, they are first converted to their trimethylsilyl derivatives by replacing the hydrogen atom of the mercapto group by a trimethylsilyl group.

European patent application No. 81.200981.9, which is not pre-published, discloses a new method for the introduction of a thio-substituent in the 3-methyl group of cephalosporanic acid derivatives by reacting a 7-acylamino-3-bromomethyl-3-cephem-4-carboxylic acid-1-oxide derivative with a trimethylsilylated thiol and these reactions proceed smoothly and with virtually quantitative yields. The method for preparing thioethers from alkylthio(trimethyl)silanes and alkyl halides requires, however, high temperatures and reaction times of up to several weeks to obtain low to moderate yields [Abel, J. Chem. Soc., 4406 (1960); Abel et al, J. Chem. Soc., 2455 (1964)]. Similarly, the reaction of arylthio(trimethyl)silanes with methyl iodide is reported to be sluggish in the presence of a solvent, even at high temperatures, and does not give the anticipated thioether in a satisfactory yield. The same holds for the reaction with benzyl bromide. Only with the very reactive phenacyl bromide could a good yield of phenacyl phenyl sulfide be obtained by heating at 60° C. for 5 hours [Kozuka et al, J. Chem. Soc., Japan, 54, 1420 (1981)].

OBJECTS OF THE INVENTION

It is an object of the invention to provide an improved process for the preparation of thioethers in good yields in a relatively short time under mild conditions.

It is another object of the invention to provide a process of the invention for improving the preparation of thioethers using hexamethylphosphoric triamide as a solvent.

These and other objects and advantages of the invention will become obvious from the following detailed description.

THE INVENTION

The novel process of the invention comprises reacting a silylated thiol of the formula

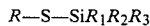

$$R-S-SiR_1R_2R_3 \qquad I$$

wherein R is an organic group and $R_1$, $R_2$ and $R_3$ are individually selected from the group consisting of alkyl of 1 to 4 carbon atoms with an organic halide, sulfate or sulfonate in the presence of hexamethylphosphoric triamide as a solvent or co-solvent.

The process of the invention is carried out under neutral conditions in aprotic solvents, thus preventing any side-reactions as may take place under the alkaline conditions prevailing in the method of the prior art discussed above. Suitable solvents are, for example, acetonitrile, dichloromethane, toluene and ethyl acetate. The process may be carried out at relatively low temperatures as compared with the prior art processes, generally at a temperature between 0° and 150° C., preferably between 20° and 80° C.

The application of hexamethylphosphoric triamide constitutes a considerable improvement over the prior art in the preparation of thioethers from trimethylsilylated thiols. It is preferred to use 0.5 to 5 equivalents of hexamethylphosphoric triamide. The process of the invention may also advantageously be used in the preparation of 7-acylamino-3-(thio-substituted)methyl-3-cephem-4-carboxylic acid 1-oxide derivatives from the corresponding 3-bromomethyl derivatives, viz. in those cases in which the trimethylsilylated thiol is of very low reactivity or when it is desirable to lower the reaction temperature or to shorten the reaction time.

The organic halide used in the process of the invention can be a chloride, bromide or iodide, but preferably is a bromide or iodide. Various types of organic halides are suitable. Examples are halides wherein the organic group is a straight or branched-chain alkyl which optionally contains an unsaturated bond, aralkyl group in which the aryl group comprises as well heteroaromatic groups such as phenyl, naphthyl, etc. and heteroaromatic groups such as thienyl, pyridyl, etc. or heterocyclic group. Each of these groups may be further substituted by one or more groups which do not interfere with the reaction between the halides and the silylated thiols of formula I.

Suitable substituents are, for example, halogen atoms, alkyl, alkoxy and alkylthio, nitro and cyano and esterified or silylated carboxyl groups. Examples of suitable halides for use in the process of the invention are halides wherein the organic group is a methyl, ethyl, isopropyl, butyl, allyl, phenyl or benzyl group, each of which may be substituted as indicated herebfore. A particularly important group of organic halides is formed by 7-acylamino-3-bromomethyl-3-cephem-4-carboxylic acid 1-oxide derivatives which are valuable intermediates in methods for the preparation of therapeutically active cephalosporins.

When two halogen atoms are present in the molecule of an organic halide, dithioethers may be formed. This is particularly the case when the organic dihalide is a dihalomethane and, to a lesser extent, when it is a 1,2-dihaloethane. It is known from the literature that the product formed by replacing one of the halogen atoms of a dihalomethane by a thio-substituent results in a product having a very high tendency to nucleophilic substitution. It is also known that even in the presence of an excess of dichloromethane the reaction of sodium p-chlorothiophenolate with dichloromethane results in the formation of only the di-substitution product, di-(chlorophenylthio)methane [Kuliev et al, Azerb. Khim. Zh. 46 (1966)]. Similar phenomena were noticed in the method of the present invention.

Suitable organic sulfates and sulfonates for use in the process of the invention are dialkyl sulfates and alkyl sulfonates, especially the alkyl esters of benzene and naphthalene sulfonic acids.

Various types of silylated thiols of formula I may be used in the process of the invention. For example, the organic group R may be an alkyl, aryl, aralkyl or heterocyclic group. Each of these groups may be further substituted by one or more groups as specified above for the organic halides. Suitable alkyl groups are straight or branched-chain alkyls; a suitable aryl group is, for example, phenyl. Suitable heterocyclics are, for example, 5- or 6-membered heterocyclic groups having one or more nitrogen or sulfur atoms as the heteroatoms. The nitrogen-heterocyclic trialkylsilylated thiols yield mainly the S-substitution products on reaction with halides, but N-substitution also was noticed.

When the organic group R contains a carboxyl, this group will be silylated as well during the process of preparing the silylated thiols of formula I from the corresponding thiols. Thus, when such a silylated thiol is reacted according to the process of the invention with an organic halide, sulfate or sulfonate, the carboxyl group is protected against undesired side-reactions. After the reaction has been completed, any silyloxycarbonyl groups present in the product, if desired, can easily be converted to free carboxyl groups by known methods. Likewise, when any free carboxyl groups are present in the organic halides used as starting materials in the process of the invention, these carboxyl groups can be protected with a silyl group before this halide is reacted with the silylated thiol.

The trialkylsilylated thiols of formula I can be prepared by a known method. Trimethylsilylated thiols are preferably prepared by the method disclosed in European patent application No. 81.200771.4 in which thiols are trimethylsilylated with 1,1,1,3,3,3-hexamethyldisilazane in the presence of a catalyst. The trimethylsilylated thiol can be isolated from the reaction mixture obtained but, more conveniently, the reaction mixture itself also can be used as a starting material in the process of the present invention.

In the following examples there are described several preferred embodiments to illustrate the invention. However, it is to be understood that the invention is not intended to be limited to the specific embodiments.

In the examples, (1) PMR spectra were recorded at 60 MHz unless otherwise stated; chemical shifts are reported relative to tetramethylsilane ($\delta=0$) used as an internal standard. (2) 13C NMR spectra were taken at 20 MHz; tetramethylsilane ($\delta=0$) was used as an internal standard. (3) IR spectra were obtained on KBr discs. (4) Boiling points and melting points are uncorrected. (5) Quantitative HPLC analysis were performed with solutions of appropriate concentrations which were prepared by standard techniques. Whenever required, the purity of the reference substance was determined by quantitative PMR analysis using an internal standard technique. The accuracy is estimated to be 5%. (6) Reactions were carried out in a dry nitrogen atmosphere and a stream of nitrogen was passed over the reaction mixture and, in case of catalyzed silylations with hexamethyldisilazane, the nitrogen was passed into water and used to determine the reaction time by titrating the ammonia generated in the reaction with 0.1 to 1.0N sulfuric acid, whichever was appropriate. Other reactions were followed by thin-layer chromatography on silicagel G. (7) Solvents used were dried over 4A molecular sieves and were of an alcohol-free grade. Solutions were dried over magnesium sulfate. (8) All evaporations were performed under reduced pressure on a rotary evaporator at a bath temperature not exceeding 35° C.

EXAMPLE 1

A solution of 171 mg (0.94 mmole) of phenylthio(trimethyl)silane in 1 ml of acetonitrile was added to a solution of 192 mg (1.12 mmole) of benzyl bromide in 1 ml of acetonitrile and 0.36 ml of hexamethylphosphoric triamide and the mixture was stirred for 1.5 hours at 50° C. Then, 2 ml of methanol were added and the solution thus obtained contained 183 mg of benzyl phenyl sulfide according to quantitative HPLC analysis which amounts to a yield of 97%. The product had a boiling point of 188°–192° C./22 mm Hg and melted at 39°–40° C.

EXAMPLE 2

(a) 0.60 ml of benzyl bromide (5.0 mmoles) were added at 50° C. to a solution of 816 mg (3.64 mmoles) of phenylthio(triethyl)silane in 5 ml of acetonitrile and 0.9 ml of hexamethylphosphoric triamide. After stirring for 45 minutes at 50° C., the reaction was quenched with 2 ml of ethanol and HPLC analysis of the diluted reaction mixture revealed the yield of benzyl phenyl sulfide to be 96%.

(b) Reaction of 949 mg (4.24 mmoles) of phenylthio(dimethyl) (t-butyl)silane with the same reagents and at the same temperature as mentioned under (a) for 15 minutes yielded 90% of benzyl phenyl sulfide.

EXAMPLE 3

A mixture of 11.52 g (63 mmoles) of phenylthio(trimethyl)silane, 22 ml of hexamethylphosphoric triamide and 18.8 ml (250 mmoles) of ethyl bromide was heated in a bath at 40° C. for 2 hours after which the conversion was complete. A solid formed in the reaction mixture and heating was continued for 1 hour after which the mixture was poured into a mixture of 150 ml of ethyl acetate and 50 ml of water. The ethyl acetate layer was separated and washed sequentially twice with 50 ml of water, 50 ml of a saturated sodium bicarbonate solution and twice with 25 ml of water. The combined water layers were extracted three times with 25 ml of ethyl acetate and the combined organic phases were washed twice with 25 ml of water, dried and evaporated to dryness. The residue was vacuum distilled to obtain 7.25 g (83% yield) of ethyl phenyl sulfide with a boiling point of 81.5°–84° C./14 mm Hg and a refractive index of $n_D^{25}=1.5632$.

EXAMPLE 4

A solution of 11.34 g (57 mmoles) of phenacyl bromide in 15 ml of acetonitrile was added to a solution of 9.51 g (52.2 mmoles) of phenylthio(trimethyl)silane in 5 ml of acetonitrile and 9.8 ml of hexamethylphosphoric triamide during which the temperature rose from 20° to 75° C. The reaction was complete within 5 minutes and by quantitative HPLC analysis, it was found that the yield of phenacyl phenyl sulfide was quantitative. The reaction mixture was worked up as described in Example 3, but the residue was crystallized from ethanol to obtain 91% of phenacyl phenyl sulfide melting at 51°–52° C.

EXAMPLE 5

6.70 g (33.6 mmoles) of phenacyl bromide were added to a mixture of 4.96 g (30.6 mmoles) of butylthio(trimethyl)silane, 6.0 ml of acetonitrile and 5.9 ml of hexamethylphosphoric triamide and after stirring for 1.5 hours at 80° C., the mixture was cooled and subjected to quantitative HPLC analysis whereby it was found that 92% of butyl phenacyl sulfide had been formed.

EXAMPLE 6

4.80 ml (77 mmoles) of methyl iodide were added to a solution of 12.87 g (70.7 mmoles) of phenylthio(trimethyl)silane in 15 ml of acetonitrile and 13.5 ml of hexamethylphosphoric triamide which caused the temperature to rise from room temperature to 90° C. After stirring for 30 minutes the reaction mixture was cooled to room temperature and a sample was taken for quantitative HPLC analysis, by which it was found that the yield of thioanisole was 98%. The acetonitrile was evaporated and the residue was treated as described in Example 3. Vacuum distillation of the residue yielded 7.89 g (90%) of thioanisole boiling at 89°–92° C./18–22 mm Hg and having a refractive index of $n_D^{25}=1.5834$.

EXAMPLE 7

3.08 g (16.6 mmoles) of methyl p-toluenesulfonate were added to a solution of 1.90 g (10.4 mmoles) of phenylthio(trimethyl)silane in a mixture of 4 ml of acetonitrile and 2 ml of hexamethylphosphoric triamide. After stirring for 1 hour at 70° C., the mixture was cooled and subjected to quantitative HPLC analysis to determine that the yield of thioanisole was 94%.

EXAMPLE 8

1.9 ml (20 mmoles) of dimethyl sulfate were added to a solution of 3.38 g (18.6 mmoles) of phenylthio(trimethyl)silane in a mixture of 7 ml of acetonitrile and 2.5 ml of hexamethylphosphoric triamide. After stirring for 2.5 hours at ambient temperature, a quantitative HPLC analysis was carried out by which it was found that the yield of thioanisole was 75%.

EXAMPLE 9

1 ml of hexamethylphosphoric triamide and 1.0 g (4.15 mmoles) of 3-bromo-4-hydroxycoumarin were added to a solution of 0.91 g (5.0 mmoles) of phenylthio(trimethyl)silane in 25 ml of dry acetonitrile. After refluxing for 1 hour, the mixture was evaporated and the residue was dissolved in 125 ml of ethyl acetate. The solution obtained was washed twice with 125 ml of water and the ethyl acetate layer was dried and evaporated to dryness. The solid residue was washed with 100 ml of heptane and then with three portions of 50% ethanol, was vacuum dried at 40° C. to obtain 0.79 g (70.5% yield) of 3-phenylthio-4-hydroxycoumarin melting at 186°–189° C.

EXAMPLE 10

A mixture consisting of 11.51 g (63.2 mmoles) of phenylthio(trimethyl)silane, 5.0 ml (77 mmoles) of bromochloromethane, 12 ml of acetonitrile and 11 ml of hexamethylphosphoric triamide was heated for 1 hour in a bath at 80° C. and then it was poured into 100 ml of ethyl acetate. The solution obtained was washed three times with 10 ml of water, three times with 10 ml of 1N potassium hydroxide solution and finally three times with 10 ml of water, dried and evaporated to dryness. After addition of 25 ml of carbon tetrachloride, the evaporation was repeated to obtain 6.95 g (94.8% yield) of di(phenylthio)methane melting at 34°–36° C.

EXAMPLE 11

1.50 g (7.0 mmoles) of 4-nitrobenzyl bromide was added to a mixture of 1.36 g (6.3 mmoles) of 4-chlorophenylthio(trimethyl)silane, 20 ml of acetonitrile and 2.3 ml of hexamethylphosphoric triamide and the conversion was complete after stirring for 5 minutes at room temperature. The reaction mixture was evaporated to dryness and the residue was dissolved in 50 ml of ethyl acetate. The solution was washed sequentially with water (twice 10 ml), 10 ml of a 1N KOH solution and water (twice 10 ml), dried and evaporated to dryness. The solid residue was washed with heptane on a sintered glass filter and the crystals obtained were vacuum dried at room temperature to obtain 1.67 g (95% yield) of 4-chlorophenyl 4-nitrobenzyl sulfide melting at 66°–68° C.

EXAMPLE 12

A mixture consisting of 12.21 g (56.5 mmoles) of 4-chlorophenylthio(trimethyl)silane, 20 ml of hexamethylphosphoric triamide and 18.7 ml (226 mmoles) of 1-bromo-2-chloroethane was heated at 60° C. and it was established that the conversion was complete after 10 minutes. After treating the reaction mixture as described in Example 3, there were obtained 10.03 g (85.7% yield) of 2-chloroethyl 4-chlorophenyl sulfide boiling at 105°–109° C./1.0 mm Hg and melting at 28°–29° C. The residue of the distillation contained 1,2-bis(4-chlorophenylthio)ethane as a by-product which after crystallization from methanol melted at 87°–88° C.

EXAMPLE 13

5.1 ml (59 mmoles) of allyl bromide were added to a mixture of 10.04 g (51.2 mmoles) of p-tolylthio(trimethyl)silane in 20 ml of acetonitrile and 18 ml of hexamethylphosphoric triamide and the conversion was complete after stirring for 20 minutes at room temperature. The reaction mixture was treated as described in Example 3 to obtain 7.1 g (85% yield) of allyl p-tolyl sulfide boiling at 110°–111° C./14 mm Hg and having a refractive index of $n_D^{25}=1.5644$.

EXAMPLE 14

5.78 g (27.5 mmoles) of trimethylsilyl bromoacetate were added to a solution of 4.85 g (25 mmoles) of p-tolylthio(trimethyl)silane in 10 ml of acetonitrile and 5 ml of hexamethylphosphoric triamide which caused a rise in temperature from 22° to 69° C. within 2 minutes. According to thin layer chromatography, the reaction was complete within 5 minutes. After evaporation of the acetonitrile, 100 ml of water were added to the residue and the solution obtained was extracted with three 50 ml portions of ethyl acetate. The combined extracts were washed with 0.1N HCl, dried, filtered and evaporated to dryness. The residue was crystallized from 30 ml of a 1:5 mixture of toluene and hexane to obtain 4.08 g (90% yield) of p-tolylthioacetic acid melting at 94.5°–95.0° C. Work-up of the mother liquor yielded another 0.31 g (6.8% yield) of material melting at 86°–89° C.

EXAMPLE 15

(a) 3,4-Dichlorophenylthio(trimethyl)silane was prepared by refluxing a mixture of 8.45 g (47 mmoles) of 3,4-dichlorothiophenol, 22 mg (0.045 mmole) of tetraphenyl imidodiphosphate, 10 ml of 1,2-dichloroethane and 7.4 ml (35 mmoles) of hexamethyldisilazane for 45 minutes and the product was isolated by distillation to obtain a 95.3% yield with a boiling point of 96°–97° C./0.8 mm Hg, and having a refractive index of $n_D^{25} = 1.5600$.

(b) 3.5 ml (55 mmoles) of chloroacetonitrile were added to a refluxing solution of 11.0 g (44 mmoles) of 3,4-dichlorophenylthio(trimethyl)silane in a mixture of 25 ml of acetonitrile and 10 ml of hexamethylphosphoric triamide and the reaction was complete with 2 minutes. The residue obtained after evaporation of the acetonitrile was dissolved in ethyl acetate, and the solution was washed with water, dried and evaporated to dryness to obtain 9.30 g (93% yield) of (3,4-dichlorophenylthio)acetonitrile boiling at 127°–130° C./0.4 mm Hg and having a refractive index of $n_D^{25} = 1.5920$.

EXAMPLE 16

4.62 g (21.3 mmoles) of 4-nitrobenzyl bromide were added to a solution of 4.60 g (19.4 mmoles) of trimethylsilyl trimethylsilylthioacetate in 10 ml of acetonitrile and 4.9 ml of hexamethylphosphoric triamide and the reaction was complete after stirring for 30 minutes at 80° C. The reaction mixture was cooled, diluted and subjected to quantitative HPLC analysis to determine that 97% of 4-nitrobenzylthioacetic acid had been formed.

EXAMPLE 17

15 ml (72 mmoles) of hexamethyldisilazane were added to a refluxing mixture of 9.9 g (75 mmoles) of 5-mercapto-2-methyl-1,3,4-thiadiazole, 27 mg (0.15 mmole) of saccharin, 50 ml of acetonitrile and 20 ml of hexamethylphosphoric triamide and after refluxing for 4.5 hours, the calculated amount of ammonia had been evolved. Refluxing was continued for 30 minutes and the mixture containing 5-trimethylsilylthio-2-methyl-1,3,4-thiadiazole was cooled to room temperature and 9.9 ml (80 mmoles) of benzyl bromide were added thereto which raised the temperature to about 50° C. All starting material was consumed within 5 minutes. The acetonitrile was removed by evaporation and 100 ml of ethyl acetate were added to the residue. The solution was poured into 250 ml of water and the aqueous layer was extracted three times with 30 ml of ethyl acetate. The combined organic extracts were washed with a 10% sodium chloride solution, dried, filtered and evaporated to dryness. The solid residue was washed with hexane containing some diethyl ether to obtain 15.91 g (96.4% yield) of 5-benzylthio-2-methyl-1,3,4-thiadiazole melting at 60°–63° C. Crystallization from a mixture of ethyl acetate and petroleum ether (boiling range 40°–60° C.) provided 14.27 g of the pure substance melting at 62.5°–63.5° C.

UV (CH$_3$CN): $\lambda_{max}$ 267 nm ($\epsilon = 6250$).

This product was used as the reference substance for the HPLC analysis mentioned herebelow and in Example 18.

(b) 2.0 mg (0.004 mmoles) of di-4-nitrophenyl N-(4-toluenesulfonyl)phosphoramidate were added to a solution of 264 mg (2 mmoles) of 5-mercapto-2-methyl-1,3,4-thiadiazole in 5 ml of toluene and 1.06 ml (6.1 mmoles) of hexamethylphosphoric triamide and then while refluxing, 0.50 ml (2.4 mmoles) of hexamethyldisilazane were added. After refluxing for 1.5 hours, the solution was evaporated to dryness and the residue was dissolved in 4 ml of acetonitrile. 0.28 (2.3 mmoles) of benzyl bromide were added to the solution and it was established that the conversion was complete after stirring for 10 minutes. HPLC analysis of the reaction mixture indicated a quantitative yield of 5-benzylthio-2-methyl-1,3,4-thiadiazole.

EXAMPLE 18

(a) 13.2 mg (100 mmoles) of 5-mercapto-2-methyl-1,3,4-thiadiazole were converted into 5-trimethylsilylthio-2-methyl-1,3,4-thiadiazole by refluxing for 1.5 hour in 75 ml of toluene with 15 ml (72 mmoles) of hexamethyldisilazane using 50 mg (0.1 mmoles) of di-4-nitrophenyl-N-(4-toluene-sulfonyl)-phosphoramidate as a catalyst. The solvent and excess hexamethyldisilazane were evaporated and the residue was dissolved in dry hexamethylphosphoric triamide.

(b) To 1 ml of this solution, which according to HPLC analysis contained 1.23 mmole of 5-trimethylsilylthio-2-methyl-1,3,4-thiadiazole, 3 ml of acetonitrile and 0.20 ml (1.68 mmole) of benzyl bromide were added and the mixture was stirred for 0.5 hour at room temperature after which, according to HPLC analysis, 1.28 mmole (104%) of 5-benzylthio-2-methyl-1,3,4-thiadiazole had been formed.

(c) To 1 ml of the solution prepared under (a), 3 ml of acetonitrile and 0.20 ml (1.74 mmole) of benzyl chloride were added and after stirring for 1.5 hour at 65° C., 1.15 mmole (93.5%) of 5-benzylthio-2-methyl-1,3,4-thiadiazole had been formed, according to HPLC analysis. There was still 8% of the starting material present in the reaction mixture.

EXAMPLE 19

A mixture consisting of 13.2 g (0.10 mole) of 5-mercapto-2-methyl-1,3,4-thiadiazole, 20 ml of toluene, 25 ml of hexamethylphosphoric triamide, 20 ml (0.096 mole) of hexamethyldisilazane and 50 mg (0.1 mmole) of di-4-nitrophenyl N-(4-toluenesulfonyl)-phosphoramidate was refluxed for 90 minutes and the mixture was then concentrated to obtain a solution of 5-trimethylsilylthio-2-methyl-1,3,4-thiadiazole in hexamethylphosphoric triamide. 15 ml of acetonitrile and 21.5 ml (0.20 mole) of butyl bromide were added thereto and the mixture was stirred for 5 hours at room temperature and then concentrated. 100 ml of water and sodium bicarbonate were added until evolution of carbon dioxide stopped and the mixture was extracted with ethyl acetate. The extract was dried, filtered and evaporated to dryness and the residue was separated by chromatography (silica gel; dichloromethane and a 95:5 mixture of dichloromethane and acetone, respectively) to obtain 0.4 g of 3-butyl-5-methyl-$\Delta^4$-1,3,4-thiadiazoline-2-thione as a by-product.

PMR (CCl$_4$): 0.8–2.0 (m, 7H); 2.39 (s, 3H); 4.15 (t, 2H, J 7.2 Hz).

$^{13}$C—NMR (CDCl$_3$): 13.4; 15.9; 19.5; 29.7; 50.4; 155.3; 185.7. and 10.9 g (58%) of 5-butylthio-2-methyl-1,3,4-thiadiazole boiling at 97°–99° C./0.6 mm Hg and having a refractive index of $n^{25} = 1.5492$.

UV (CH$_3$CN): $\lambda_{max}$ 266 nm ($\epsilon = 7000$).

PMR(CDCl$_3$): 0.8–2.0 (m, 7H); 2.70 (s, 3H); 3.27 (t, 2H, J 7.4 Hz).

—C—NMR (CDCl$_3$): 13.6; 15.1; 21.4; 30.8; 33.5; 164.2; 165.4.

EXAMPLE 20 by HPLC analysis. The results are summarized in the following table.

| TMT (mmoles) | CH$_3$CH=CH$_2$X (mmoles) | HMPT (ml) | solvent (10 ml) | temperature (°C.) | reaction time (min.) | yield (%) |
|---|---|---|---|---|---|---|
| 7.2 | 8.5 (X=Br) | 1.5 | CH$_3$CN | 20 | 90 | 99 |
| 9.7 | 11.6 (X=Br) | 2.0 | CH$_3$CN | 45 | 45 | 100 |
| 7.7 | 9.1 (X=Br) | 1.6 | CH$_2$Cl$_2$ | 45 | 90 | 97 |
| 9.3 | 10.8 (X=Cl) | 1.9 | CH$_3$CN | 45 | 240 | 93 |

(a) Using the procedure of Example 19, 1.32 g (10 mmoles) of 5-mercapto-2-methyl-1,3,4-thiadiazole were silylated with 2.6 ml (15 mmoles) of hexamethyldisilazane in 10 ml of toluene and 2.6 ml of hexamethylphosphoric triamide using 5 mg (0.027 mmole) of saccharin as a catalyst by refluxing for 1.5 hour. After concentration by evaporation, 5 ml of acetonitrile were added thereto and the solution obtained was heated at 50° C. while 2.1 ml (20 mmoles) of butyl bromide were added. The conversion was complete after stirring for 3 hours at this temperature and according to quantitative HPLC analysis, there had been formed 8.91 mmoles (89.1%) of 5-butylthio-2-methyl-1,3,4-thiadiazole, while 5.3% of 3-butyl-5-methyl-$\Delta^4$-1,3,4-thiadiazoline-2-thione was found as a by-product.

(b) The experiment was repeated, using instead of butyl bromide, 2.3 ml (20 mmoles) of butyl iodide which were added while stirring was effected at room temperature and the conversion was complete after 3 hours. By quantitative HPLC analysis, it was established that the yield of 5-butylthio-2-methyl-1,3,4-thiadiazole was 89.1% while less than 1.3% of said by-product had been formed.

EXAMPLE 21

1.85 ml (22 mmoles) of chloromethyl methyl sulfide were added to a refluxing solution of 4.18 g (20.5 mmoles) of 5-trimethylsilylthio-2-methyl-1,3,4-thiadiazole in a mixture of 15 ml of acetonitrile and 3.85 ml of hexamethylphosphoric triamide and after refluxing for 10 minutes, the reaction was complete. 5 ml of ethanol were added thereto and the mixture was evaporated to dryness. The residue was dissolved in ethyl acetate and the solution obtained was extracted with dilute sodium hydroxide solution (pH 10) and with water. The ethyl acetate layer was dried and evaporated to dryness and the residue contained two components which were separated by chromatography over silica gel using a 10% solution of acetone in dichloromethane as an eluent. From the first fractions, 0.23 g (5.8%) of 3-methylthiomethyl-5-methyl-$\Delta^4$-1,3,4-thiadiazoline-2-thione was isolated as a by-product.

PMR (CDCl$_3$): 2.34 (s, 3H); 2.50 (s, 3H); 5.35 (s, 2H).

From the following fractions, 3.60 g (91.4%) of 5-(methylthio)-methylthio-2-methyl-1,3,4-thiadiazole were isolated with a boiling point of 115°–116° C./0.4 mm Hg and having a refractive index of n$_D^{25}$=1.6222.

PMR (CDCl$_3$): 2.29 (s, 3H); 2.76 (s, 3H); 4.41 (s, 2H).

EXAMPLE 22

5-trimethylsilylthio-2-methyl-1,3,4-thiadiazole (TMT) was reacted with allyl chloride and with allyl bromide under various conditions in the presence of hexamethylphosphoric triamide (HMPT) and yields of 5-allylthio-2-methyl-1,3,4-thiadiazole were determined by HPLC analysis. The results are summarized in the following table.

The reference compound which was isolated by distillation from a run without HMPT boiled at 102° C./1.0 mm Hg.

UV (CH$_3$CN): $\lambda_{max}$ 265 nm ($\epsilon$=6500).

PMR (CDCl$_3$): 2.65 (s, 3H), 3.83 and 3.94 (d, 2H), 5.05–6.35 (m, 3H).

EXAMPLE 23

50 ml of hexane and 48 mg (0.1 mmole) of tetraphenyl imidodiphosphate were added to a solution of 2.56 g (20 mmoles) of 1-phenyl-5-mercapto-1H-tetrazole in 5 ml of hexamethylphosphoric triamide and the mixture was refluxed while 8.3 ml (40 mmoles) of hexamethyldisilazane were added whereupon a precipitate was formed. After addition of 25 ml of ethyl acetate, refluxing was continued for 2 hours and then the mixture was evaporated to dryness at 40° C. under oil pump vacuum. The 1-phenyl-5-trimethylsilylthio-1H-tetrazole thus obtained was dissolved in 45 ml of acetonitrile and then, 4.75 g (22 mmoles) of 4-nitrobenzyl bromide were added to the solution which immediately resulted in the formation of a precipitate. After stirring for 15 minutes at room temperature, the mixture was evaporated and the residue was dissolved in a mixture of 50 ml of water and 50 ml of ethyl acetate. The ethyl acetate layer was separated, washed three times with 10 ml of water, dried, filtered and evaporated to dryness. The residue was crystallized from 80 ml of 1:1 mixture of ethyl acetate and heptane to obtain 4.23 g (67.6% yield) of 1-phenyl-5-(4-nitrobenzyl)-thio-1H-tetrazole melting at 153°–154° C.

UV (CH$_3$CN): $\lambda_{max}$ 264 nm ($\epsilon$=13,000).

PMR (CDCl$_3$): 4.71 (s, 2H); 7.54 (s, 5H); 7.72 and 8.24 (ABq, 4H, J 9 Hz).

This product was used as the reference substance for the HPLC analysis mentioned in Examples 24 and 25.

EXAMPLE 24

264.5 mg (1.49 mmoles) of 1-phenyl-5-mercapto-1H-tetrazole were suspended in a mixture of 15 ml of chloroform and 15 ml of 1,2-dichloroethane and 2 mg (0.01 mmole) of saccharin were added thereto. While refluxing 0.65 ml (3.1 mmoles) of hexamethyldisilazane were added to the mixture which was refluxed for 1 hour and was evaporated to dryness. The residue dissolved in 10 ml of acetonitrile and 0.3 ml of hexamenthylphosphoric triamide and 0.35 g (1.62 mmole) of 4-nitrobenzyl bromide was added to the solution obtained which resulted immediately in the formation of a solid. After stirring for 10 minutes at room temperature, quantitative HPLC analysis was carried out to confirm a yield of 95% of 1-phenyl-5-(4-nitrobenzyl)-thio-1H-tetrazole.

EXAMPLE 25

Using the procedure of Example 23, 2.60 g (14.6 mmoles) of 1-phenyl-5-mercapto-1H-tetrazole were silylated in 75 minutes with 7.5 ml (36 mmoles) of hexamethyldisilazane in a mixture of 30 ml of chloroform and 30 ml of 1,2-dichloroethane using 19 mg (0.1 mmole) of saccharin as a catalyst. After evaporation to dryness, the residue was dissolved in acetonitrile and 5 ml of this solution containing 0.72 mmole of 1-phenyl-5-trimethylsilylthio-1H-tetrazole were added to a solution of 0.17 g (0.79 mmole) of 4-nitrobenzyl bromide in 0.17 ml of hexamethylphosphoric triamide and also to a solution of 0.13 g (0.76 mmole) of 4-nitrobenzyl chloride in 0.17 ml of hexamethylphosphoric triamide. After stirring for 1 hour, the reactions were quenched with 1 ml of methanol and the yields of product determined by HPLC analysis. The yields of 1-phenyl-5-(4-nitrobenzyl)-thio-1H-tetrazole were 102% and 98%, respectively

EXAMPLE 26

(a) 3.75 ml (18 mmoles) of hexamethyldisilazane were added at reflux to a solution of 2.83 g (24.4 mmoles) of 5-mercapto-1-methyl-1H-tetrazole and 50 mg (0.28 mmole) of saccharin in 30 ml of acetonitrile and after refluxing for 90 minutes, the reaction mixture was evaporated to dryness to obtain 1-methyl-5-trimethylsilylthio-1H-tetrazole as a liquid with a refractive index $n_D^{25} = 1.5175$.

PMR (CCl4): 0.81 (s, 9H); 3.79 (s, 3H).

(b) The said product was dissolved in a mixture of 10 ml of acetonitrile and 5 ml of hexamethylphosphoric triamide and 2.75 ml (27.5 mmoles) of isopropyl iodide were added to this solution. The mixture was stirred for 90 minutes at room temperature, after which the acetonitrile was evaporated. 25 ml of ethyl acetate and 25 ml of water were added to the residue and the pH was adjusted to 10.0 with 1N sodium hydroxide solution. The decanted ethyl acetate layer was washed with 25 ml of sodium hydroxide solution of pH 10.0 and 25 ml of water, dried and evaporated to dryness. The 4.30 g of residue were further purified by chromatography over 150 g of silica gel using ethyl acetate as an eluent. After evaporation of the appropriate fractions, 3.04 g (80% yield) of 5-isopropylthio-1-methyl-1H-tetrazole with a refractive index of $n_D^{25} = 1.5030$ were obtained.

PMR (CDCl3): 1.50 (d, 6H, J 6.0 Hz); 3.98 (s, 3H); 4.05 (q, 1H, J 6.0 Hz).

EXAMPLE 27

(a) 1.62 g (8.1 mmoles) of phenacyl bromide were added to a solution of 1.90 g (7.76 mmoles) of 1-trimethylsilyl-3-trimethylsilylthio-1H-1,2,4-triazole in 10 ml of acetonitrile and 1.55 ml of hexamethylphosphoric triamide and the reaction was complete after stirring for 15 minutes at room temperature. The precipitate formed after the addition of 4 ml of methanol was filtered off and was washed with diethyl ether and with hexane to obtain a yield of 1.85 g (79.5%) of 3-phenacylthio-1H-1,2,4-triazole hydrobromide melting at 201.5°–202° C. (dec.). A second crop of 0.3 g (13%) melting at 191°–192° C. (dec.)) was isolated from the mother liquor. 0.90 g of this salt was taken up in 10 ml of water which was layered with 20 ml of ethyl acetate. The pH was adjusted to 9 with 1N potassium hydroxide and the free base was extracted from the water layer with ethylacetate to obtain 0.66 g (100% yield) of 3-phenacylthio-1H-1,2,4-triazole melting at 119°–120° C. Crystallization from ethyl acetate raised the melting point to 120°–121° C.

PMR (DMSO-d6): 4.87 (s, 2H); 7.4–8.3 (m, 6H); 8.53 (s, 1H).

IR: 3145, 1699, 1660, 1593, 1578, 1485 cm$^{-1}$.

(b) 1-trimethylsilyl-3-trimethylsilylthio-1H-1,2,4-triazole was prepared by adding 29.2 ml (140 mmoles) of hexamethyldisilazane to a refluxing suspension of 9.70 g (96 mmoles) of 3-mercapto-1H-1,2,4-triazole and 100 mg (0.25 mmole) of di-4-nitrophenyl-N-(4-toluenesulfonyl)-phosphoramidate in 200 ml of dichloromethane and the calculated amount of ammonia was evolved after refluxing for 75 minutes. Refluxing was continued for 30 minutes and then the clear solution obtained was evaporated to dryness to obtain 23.1 g (98% yield) of 1-trimethylsilyl-3-trimethylsilylthio-1H-1,2,4-triazole melting at 90°–94° C.

PMR (CCl4): 0.52 (s, 9H); 0.55 (s, 9H); 7.52 (s, 1H).

EXAMPLE 28

A mixture consisting of 2.85 g (25 mmoles) of 1-methyl-2-mercaptoimidazole, 22 mg (0.12 mmoles) of saccharin, 20 ml of toluene and 5.2 ml (25 mmoles) of hexamethyldisilazane was refluxed for 1 hour and after cooling to room temperature, 5.40 g (25 mmoles) of 4-nitrobenzyl bromide and then 5 ml of hexamethylphosphoric triamide were added to the mixture which contained 1-methyl-2-(trimethylsilylthio)-imidazole. After stirring for 2 hours at room temperature, the mixture was diluted to 150 ml with ethyl acetate and the solution thus obtained was washed three times with 50 ml of a saturated sodium bicarbonate solution and then twice with 20 ml of water. The organic layer was dried, filtered and evaporated to dryness and the crystalline residue was washed with 100 ml of petroleum ether (boiling range 60°–80° C.) and then vacuum dried to obtain 5.54 g (89% yield) of 1-methyl-2-(4-nitrobenzylthio)-imidazole melting to 74°–77° C. Crystallization of a sample from ethanol raised the melting point to 77.5°–78.0° C.

EXAMPLE 29

A solution of 1-methyl-2-(trimethylsilylthio)-imidazole was prepared by refluxing a mixture of 1.16 g (10 mmoles) of 1-methyl-2-mercaptoimidazole, 18 mg (0.1 mmole) of saccharin, 1.5 ml (7.2 mmoles) of hexamethyldisilazane and 25 ml of acetonitrile for one hour. 1.8 ml of hexamethylphosphoric triamide and 2.3 g (10.5 mmoles) of 4-nitrobenzyl bromide were added and refluxing was continued for 10 minutes. The acetonitrile was evaporated and 100 ml of ethyl acetate were added to the residue. The crystals were filtered off and washed with ethyl acetate to obtain 2.93 g (88.8% yield) of 1-methyl-2-(4-nitrobenzylthio)-imidazole hydrobromide melting at 183°–185° C. The filtrate was washed with water, dried and evaporated to dryness and diethyl ether was added to the residue and the mixture was filtered to obtain 0.3 g (12% yield) of 1-methyl-3-(4-nitrobenzyl)-1,2-dihydroimidazole-2-thione as a by-product melting at 162°–168° C. Crystallization from a mixture of chloroform and carbon tetrachloride raised the melting point of 167°–168° C.

PMR (DMSO-d6): 3.32 (s, 2H); 5.31 (s, 3H); 7.14 (s, 2H); 7.35, 7.49, 8.04 and 8.19 (4s, 4H);

IR: 3160, 3124, 3100, 3067, 1606, 1598, 1570, 1510, 1340 cm$^{-1}$.

EXAMPLE 30

0.20 ml (0.96 mmole) of hexamethyldisilazane was added to a suspension of 0.50 g of 7-phenylacetamido-3-bromomethyl-3-cephem-4-carboxylic acid-1-oxide with a content of 86% (1 mmole) in 10 ml of dichloromethane and the mixture was stirred for 45 minutes. To the clear solution obtained, 0.25 ml of hexamethylphosphoric triamide and 0.36 g (1.66 mmole) of 4-chlorophenylthio-(trimethyl)-silane was added and after stirring for 30 minutes at room temperature, the reaction was quenched by the addition of 2 ml of methanol which resulted in the formation of a precipitate. The mixture was evaporated to dryness and then, 20 ml of diethyl ether were added thereto. The mixture was filtered and the solid product was washed with 10 ml of diethyl ether, 10 ml of 0.1N HCl and twice with 10 ml of diethyl ether. The product was vacuum dried at room temperature to obtain 0.48 g of 7-phenylacetamido-3-(4-chlorophenyl)-thiomethyl-3-cephem-4-carboxylic acid 1-oxide with a purity of 97% according to quantitative PMR analysis (95% yield).

PMR (DMSO-d6): 3.49, 3.75, (ABq, 2H, J 15 Hz); 3.79, 4.39 (ABq, 2H, J 13.5 Hz); 3.84 (s, 2H); 4.87 (d, 1H, 4.5 Hz); 5.77 (dd, 1H, J 4.5 and 8 Hz); 7.30 (s, 4H); 7.38 (s, 5H); 8.39 (d, 1H, J 8 Hz).

IR: 3270, 1774, 1765, 1723, 1658, 1520, 1240, 1010, 997 cm$^{-1}$.

Various modifications of the process of the invention may be made without departing from the spirit or scope thereof and it is to be understood that the invention in intended to be limited only as defined in the appended claims.

What is claimed is:

1. A process for the preparation of thioethers comprising reacting a silylated thiol of the formula $$R-S-SiR_1R_2R_3 \qquad \text{I}$$

wherein R is an organic group and $R_1$, $R_2$ and $R_3$ are individually selected from the group consisting of alkyl of 1 to 4 carbon atoms with an organic chloride, bromide, iodide, sulfate or sulfonate in the presence of hexamethylphosphoric triamide as a solvent or co-solvent.

2. The process of claim 1 wherein the reaction is carried out under neutral conditions in aprotic solvents.

3. The process of claim 1 wherein the reaction is carried out at a temperature between 0° and 150° C.

4. The process of claim 1 wherein the reaction is carried out at a temperature between 20° and 80° C.

5. The process of claim 1 wherein the organic group of the halide is a straight or branched-chain alkyl or alkylene, an aralkyl group or a heterocyclic group, each of which group may be further substituted by at least one group which does not interfere with the reaction.

6. The process of claim 1 wherein the organic sulfate is dialkyl sulfate.

7. The process of claim 1 wherein the organic sulfonate is an alkyl sulfonate.

8. The process of claim 7 in which the alkyl sulfonate is an alkyl ester of benzene or naphthalene sulfonic acid.

9. The process of claim 1 wherein R is an alkyl, aryl, aralkyl or heterocyclic, each of which group may be further substituted by at least one group which does not interfere with the reaction.

10. The process of claim 9 wherein the heterocyclic group is a 5- or 6-membered group having at least one nitrogen or sulfur atom as the heteroatom.

* * * * *